United States Patent
Hampel et al.

(10) Patent No.: US 10,822,637 B2
(45) Date of Patent: Nov. 3, 2020

(54) METHOD FOR DETECTING MOLECULAR INTERACTIONS USING AN IMMOBILIZED NUCLEIC ACID

(71) Applicant: DYNAMIC BIOSENSORS GMBH, Martinsried (DE)

(72) Inventors: Paul Hampel, Germering (DE); Johannes Reusch, Munich (DE); Ulrich Rant, Munich (DE); Ralf Strasser, Munich (DE)

(73) Assignee: DYNAMIC BIOSENSORS GMBH, Martinsried (DE)

( * ) Notice: Subject to any disclaimer, the term of this patent is extended or adjusted under 35 U.S.C. 154(b) by 79 days.

(21) Appl. No.: 15/764,967

(22) PCT Filed: Sep. 29, 2016

(86) PCT No.: PCT/EP2016/073274
§ 371 (c)(1),
(2) Date: Mar. 30, 2018

(87) PCT Pub. No.: WO2017/055463
PCT Pub. Date: Apr. 6, 2017

(65) Prior Publication Data
US 2018/0274006 A1    Sep. 27, 2018

(30) Foreign Application Priority Data
Oct. 1, 2015 (EP) .................. 15187921

(51) Int. Cl.
*C12Q 1/6804* (2018.01)
*G01N 21/64* (2006.01)
(Continued)

(52) U.S. Cl.
CPC ......... *C12Q 1/6804* (2013.01); *C12Q 1/6825* (2013.01); *G01N 21/6428* (2013.01);
(Continued)

(58) Field of Classification Search
None
See application file for complete search history.

(56) References Cited

U.S. PATENT DOCUMENTS

| 2006/0148103 A1* | 7/2006 | Chen ................. B82Y 5/00 436/524 |
| 2010/0167301 A1 | 7/2010 | Collier et al. |

(Continued)

FOREIGN PATENT DOCUMENTS

| WO | WO 2010/059820 A1 | 5/2010 |
| WO | WO 2013/070990 A1 | 5/2013 |

(Continued)

OTHER PUBLICATIONS

Anonymous, "SwitchSENSE Technology from Dynamic Biosensors," Dynamic—biosensors.com accessed at http://www.dynamic-biosensors.com/images/dynamicbiosensors_switchsense.pdf, accessed on Sep. 10, 2018, 3 pages.

(Continued)

*Primary Examiner* — Melanie Brown
(74) *Attorney, Agent, or Firm* — Sterne, Kessler, Goldstein & Fox P.L.L.C.

(57) ABSTRACT

The present invention relates to a method for detecting and/or characterizing molecular interactions between two molecules, in particular two proteins and most particular between an antigen and an antibody by using an immobilized single-stranded nucleic acid molecule to which single-stranded nucleic acid molecules having a ligand attached thereto are hybridized.

14 Claims, 4 Drawing Sheets
Specification includes a Sequence Listing.

(51) Int. Cl.
| | |
|---|---|
| G01N 33/543 | (2006.01) |
| C12Q 1/6825 | (2018.01) |
| G01N 33/68 | (2006.01) |
| G01N 33/58 | (2006.01) |
| G01N 27/327 | (2006.01) |

(52) U.S. Cl.
CPC ..... *G01N 33/54353* (2013.01); *G01N 33/582* (2013.01); *G01N 33/68* (2013.01); *G01N 27/3276* (2013.01); *G01N 2021/6439* (2013.01); *G01N 2458/10* (2013.01)

(56) References Cited

U.S. PATENT DOCUMENTS

| | | | |
|---|---|---|---|
| 2014/0102915 A1 | 4/2014 | Hu et al. | |
| 2014/0248710 A1* | 9/2014 | Heyduk | G01N 33/5308 436/501 |
| 2016/0291007 A1* | 10/2016 | Kozlov | G01N 33/54306 |

FOREIGN PATENT DOCUMENTS

| | | |
|---|---|---|
| WO | WO 2015/150482 A1 | 10/2015 |
| WO | WO 2017/055463 A1 | 4/2017 |

OTHER PUBLICATIONS

Drake, AW., et al., "Biacore surface matrix effects on the binding kinetics and affinity of an antigen/antibody complex," Anal. Biochem 429:58-69, Elsevier, Netherlands (2012).

Fujiwara, K., et al., "Sandwich enzyme immunoassay of tumor-associated antigen sialosylated Lewisx using beta-D-galactosidase coupled to a monoclonal antibody of IgM isotype," J Immunol. Methods 112:77-83, Elsevier, Netherlands (1988).

Hearty, S., et al., "Measuring antibody-antigen binding kinetics using surface plasmon resonance," Methods Mol. Med. 907:411-42, Springer Publishing, Germany (2012).

Hegner, M., et al., "Immobilizing DNA on gold via thiol modification for atomic force microscopy imaging in buffer solutions," FEBS 336(3):452-56, Elsevier, Netherlands (1993).

Heyduk, E., et al., "Molecular pincers: antibody-based homogenous protein sensors," Analytical Chemistry 80(13):5152-5159, ACS Publishers, United States (2008).

International Search Report for International Application No. PCT/EP2016/073274, European Patent Office, Netherlands dated Jan. 13, 2017.

Hu, J. et al., "Quantitation of Femtomolar protein levels via direct readout with the electrochemical proximity assay," J Am. Chem. Soc. 134(16):7066-72, American Chemical Society, United States (2012).

Kaiser W., and Rant, R., "Conformations of end-tethered DNA molecules on gold surfaces: influences of applied electrical potential, electrolyte screening, and temperature," J. Am. Chem. Soc. 132:7935, American Chemical Society, United States (2010).

Knezevic, J., et al., "Quantitation of affinity, avidity, and binding kinetics of protein analytes with a dynamically switchable biosurface," J Am. Chem. 134(37):15225-15228, American Chemical Society, United States (2012).

Langer, A., et al., "Protein analysis by time-resolved measurements with an electro-switchable DNA chip," Nature Communications 4:2099, MacMillan Publishers, England (2013).

Peeters, JM., et al., "Comparison of four bifunctional reagents for coupling peptides to proteins and the effect of the three moieties on the immunogenicity of the conjugates," J Immunol Methods 120:133-143, Elsevier, Netherlands (1989).

Piliarik, M., et al., "Surface plasmon resonance biosensor for parallelized detection of protein biomarkers in dilutes blood plasma," Biosensors and Bioelectronics 26(4):1656-1661, Elsevier, Netherlands (2010).

Rant, U., et al., "Detection and Size analysis of proteins with switchable DNA layers," Nano Letters 9:1290-95, American Chemical Society, United States (2009).

Vancott, TC., "Analysis of antibody-antigen using surface plasmon resonance," Methods Mol Med. 17:273-82, Springer Publishing, Germany (1999).

International Preliminary Report on Patentability and Written Opinion for International Application No. PCT/EP2016/073274, European Patent Office, Netherlands dated Apr. 3, 2018.

\* cited by examiner a)

b)

a)

b)

METHOD FOR DETECTING MOLECULAR INTERACTIONS USING AN IMMOBILIZED NUCLEIC ACID

REFERENCE TO SEQUENCE LISTING SUBMITTED ELECTRONICALLY

The content of the sequence listing, file name "Sequence listing as filed on 29 Sep. 2016.txt"; size 803 bytes, which was electronically submitted on Sep. 29, 2016 together with the PCT application, is incorporated herein by reference in its entirety.

FIELD OF THE INVENTION

The present invention relates to a method for detecting and/or characterizing molecular interactions between two molecules, in particular two proteins and most particular between an antigen and an antibody by using an immobilized single-stranded nucleic acid molecule to which single-stranded nucleic acid molecules having a ligand attached thereto are hybridized.

BACKGROUND OF THE INVENTION

In recent years, the use of therapeutic antibodies for the treatment of diseases such as cancer and autoimmune diseases has become increasingly important. In the development of these antibodies a thorough analysis of their binding characteristics and their interaction with their binding target is necessary.

The development of therapeutic monoclonal antibodies (mAbs) requires the measurement of kinetic binding properties of antigen/antibody complexes. Accurate and precise kinetic measurements for determination of the rate constants $k_{on}$, $k_{off}$, as well as dissociation constant $K_d$ provide information about the antibody properties. The $K_d$ may affect the efficacy of the mAb, influence the pharmacokinetics and dosing strategy, and/or influence the final drug cost given that tighter binding mAbs usually enable lower doses (Drake et al. (2012) Anal. Biochem. 429: 58-69). One commonly employed method to characterize the interaction of an antibody with its target is surface plasmon resonance (SPR) in which one interactant of an interacting pair is immobilized on a gold-coated glass slide which is mounted on a prism and the other interactant is induced to flow across this surface in an aqueous buffer solution. When light passes through the prism and onto the gold surface at angles and wavelengths near the so-called "surface plasmon resonance" condition, the optical reflectivity of the gold changes when biomolecules are bound to the gold surface. By monitoring this reflectivity change the extent of interaction between the interactant on the gold surface and its binding partner in the aqueous buffer solution can be detected and quantified (Vancott (1999) Methods Mol. Med. 17: 273-282; Hearty et al. (2012) Methods Mol. Biol. 907: 411-442).

A further process for characterizing the interaction of an antibody with its target is bio-layer interferometry which analyzes the interference pattern of white light reflected by two surfaces, i.e. a layer of immobilized protein on the biosensor tip and and internal reference layer. If a ligand binds to the protein immobilized on the biosensor tip a wavelength shift occurs which can be detected.

Another recently developed technique is the "switch-SENSE" technology which is based on the electrical actuation of nucleic acid double strands to which an interactant is attached at high frequency on microelectrodes. The orientation of the nucleic acid double strands is then monitored by time-resolved single photon counting. If an analyte binds to the interactant attached to the nucleic acid double strand, the switching dynamics of the double strand is slowed down in a characteristic, detectable way (Rant et al., Nano Letters, 2009, Vol. 9, 1290-1295; Knezevic et al. (2012) J. Am. Chem. Soc. 134(37): 15225-15228; Langer et al. (2013) Nature Communications 4: 2099).

In the above methods using surface biosensors the interactant which is immobilized on the biosensor surface is typically randomly distributed, leading to differences in the local density of the interactant on the surface. Due to these differences the spatial arrangement on the surface of interactants such as antigens which bind to an antibody to be analyzed cannot be controlled. Consequently, when bivalent or bispecific antibodies are analyzed, a certain percentage of the antibodies will bind the antigen via only one Fab arm, if at the binding site no second antigen is available for binding, while another percentage of the antibodies will bind the antigen via both Fab arms, if two antigens are located close to each other on the biosensor surface so that the antibody can bind to both of them. This heterogenous mixture of antibodies bound via one Fab arm and via two Fab arms leads to complex signals which are difficult to analyze.

International patent application WO 2015/150482 A1 discloses a method for detecting and/or analyzing molecular interactions in which a stem-loop structure hybridizes with at least one single-stranded nucleic acid molecule to which at least one ligand is attached and is subsequently contacted with a sample of the binding partner which is to be analyzed.

Nevertheless, there is still a need for a simple system which enables an exact control of the distance between antigens and therefore an exact analysis of the binding behavior of complex molecules such as bivalent and bispecific antibodies.

SUMMARY OF THE INVENTION

The object of the present invention is solved by the subject-matter of the independent claims. Further embodiments and advantages of the invention are incorporated in the dependent claims.

The present invention provides a method for detecting and/or characterizing molecular interactions between a ligand and its binding partner comprising:
a) providing a nucleic acid structure comprising
  (i) a single-stranded nucleic acid molecule which is immobilized on a solid substrate; and
  (ii) at least a first and a second single-stranded nucleic acid molecule each of which forms a double strand with a part of the immobilized single-stranded nucleic acid molecule, wherein a first ligand is attached to the first single-stranded nucleic acid molecule and a second ligand is attached to the second single-stranded nucleic acid molecule; or at least one single-stranded nucleic acid molecule which forms a double strand with at least a part of the immobilized single-stranded nucleic acid molecule and to which a first and a second ligand are attached at different locations;
b) contacting the nucleic acid structure with a sample of the binding partner which is to be analyzed; and
c) detecting and/or characterizing the interaction between the ligand and the binding partner.

Exemplary nucleic acid structures which can be used in the method of the present invention are illustrated in FIG. 1.

In another embodiment the present invention provides a method for detecting and/or characterizing molecular interactions between a ligand and its binding partner comprising:
a) providing a nucleic acid structure comprising
   (i) a single-stranded nucleic acid molecule which is immobilized on a solid substrate and which does not contain repetitive sequences; and
   (ii) at least a first and a second single-stranded nucleic acid molecule each of which forms a double strand with a part of the immobilized single-stranded nucleic acid molecule, wherein a first ligand is attached to the first single-stranded nucleic acid molecule and a second ligand is attached to the second single-stranded nucleic acid molecule; or at least one single-stranded nucleic acid molecule which forms a double strand with at least a part of the immobilized single-stranded nucleic acid molecule and to which a first and a second ligand are attached at different locations;
b) contacting the nucleic acid structure with a sample of the binding partner which is to be analyzed so that the ligands and the binding partner can interact; and
c) detecting and/or characterizing the interaction between the ligand and the binding partner.

In still another embodiment the present invention provides a method for detecting and/or characterizing molecular interactions between a ligand and its binding partner comprising:
a) contacting at least a first and a second single-stranded nucleic acid molecule each of which forms a double strand with a part of the immobilized single-stranded nucleic acid molecule, wherein a first ligand is attached to the first and a second single-stranded nucleic acid molecule and a second ligand is attached to the second single-stranded nucleic acid molecule; or at least one single-stranded nucleic acid molecule which forms a double strand with at least a part of the immobilized single-stranded nucleic acid molecule and to which a first and a second ligand are attached at different locations
   with a sample of the binding partner which is to be analyzed, thereby providing a first mixture;
b) contacting the first mixture with a single-stranded nucleic acid molecule which is immobilized on a solid substrate and allowing the at least first and second single-stranded nucleic acid molecules or the at least one single-stranded nucleic acid molecule to form a double-strand with a part of the immobilized single-stranded nucleic acid molecule; and
c) detecting and/or characterizing the interaction between the ligand and the binding partner.

In yet another embodiment the present invention provides a method for detecting and/or characterizing molecular interactions between a ligand and its binding partner comprising:
a) contacting at least a first and a second single-stranded nucleic acid molecule each of which is capable of forming a double strand with a part of an immobilized single-stranded nucleic acid molecule, wherein a first ligand is attached to the first and a second single-stranded nucleic acid molecule and a second ligand is attached to the second single-stranded nucleic acid molecule; or
   at least one single-stranded nucleic acid molecule which is capable of forming a double strand with at least a part of an immobilized single-stranded nucleic acid molecule and to which a first and a second ligand are attached at different locations
   with a sample of the binding partner which is to be analyzed, thereby providing a first mixture;
b) contacting the first mixture with a single-stranded nucleic acid molecule which is immobilized on a solid substrate and which does not contain repetitive sequences and allowing the at least first and second single-stranded nucleic acid molecules or the at least one single-stranded nucleic acid molecule to form a double-strand with a part of the immobilized single-stranded nucleic acid molecule; and
c) detecting and/or characterizing the interaction between the ligand and the binding partner.

In one embodiment the first and the second ligand are the same.

In an alternative embodiment the first ligand is different from the second ligand.

Preferably, the first and the second ligand is an antigen and the binding partner is an antibody specific for said antigen and more preferably the antigen attached to the first single-stranded nucleic acid molecule is different from the antigen attached to the second single-stranded nucleic acid molecule and the antibody is a bispecific antibody.

In one embodiment the first and/or the second ligand are a protein or a part thereof or a small molecule.

In one embodiment the immobilized single-stranded nucleic acid molecule is labeled with a fluorescent dye.

In one embodiment the solid substrate has at least one electrode, the immobilized single-stranded nucleic acid molecule is labeled with a fluorescent dye and the interaction is detected and/or characterized by the steps of:
d) applying an external electrical field to the electrode to cause a movement of said combination product;
e) observing a signal of the label during said movement of the double strand; and
f) using the observed signal for detecting an interaction of the binding partner with the at least one ligand.

In another embodiment the solid substrate has a surface from which light is reflected and the interaction is detected and/or characterized by the steps of:
d) applying light to the surface;
e) measuring the intensity, angle, or spectrum of the reflected light; and
f) detecting an interaction of the binding partner with the first and the second ligand by observing a signal change in the intensity, angle, or spectrum of the reflected light.

The present invention also relates to a method for detecting and/or characterizing interactions between an antibody and its cognate antigen(s) comprising:
a) providing a nucleic acid structure comprising
   (i) a single-stranded nucleic acid molecule which is immobilized on a solid substrate; and
   (ii) at least a first and a second single-stranded nucleic acid molecule each of which forms a double strand with a part of the immobilized single-stranded nucleic acid molecule, wherein a first antigen is attached to the first single-stranded nucleic acid molecule and a second antigen is attached to the second single-stranded nucleic acid molecule; or at least one single-stranded nucleic acid molecule which forms a double strand with at least a part of the immobilized single-stranded nucleic acid molecule and to which a first and a second antigen are attached at different locations;
b) contacting the nucleic acid structure with a sample of the antibody which is to be analyzed; and
c) detecting and/or characterizing the interaction between the antigen(s) and the antibody.

The single-stranded nucleic acid molecule which is immobilized on a solid substrate may not contain repetitive sequences.

In one embodiment the solid substrate has at least one electrode, the immobilized single-stranded nucleic acid molecule is labeled with a fluorescent dye and the interaction is detected and/or characterized by the steps of:

d) applying an external electrical field to the electrode to cause a movement of said combination product;
e) observing a signal of the label during said movement of the double strand; and
f) using the observed signal for detecting an interaction of the binding partner with the at least one ligand.

In another embodiment the solid substrate has a surface from which light is reflected and the interaction is detected and/or characterized by the steps of:

d) applying light to the surface;
e) measuring the intensity, angle, or spectrum of the reflected light; and
f) detecting an interaction of the binding partner with the first and the second ligand by observing a signal change in the intensity, angle, or spectrum of the reflected light.

Preferably, the first antigen is different from the second antigen and the antibody is a bispecific antibody.

In one embodiment the ligand is a protein or a part thereof.

In one embodiment the immobilized single-stranded nucleic acid molecule is labeled with a fluorescent dye.

In other words, a method for detecting the interaction of the binding partner with the at least one ligand with oscillating molecules is presented. In this context, the oscillating molecules shall be understood as the nucleic acid structure comprising the immobilized single-stranded nucleic acid molecule and the first and second single-stranded nucleic acid molecules hybridized thereto. Thus, the oscillating molecules are the molecules of the moved nucleic acid structure. Said nucleic acid structure can be switched by means of the external electrical field from a lying state into a standing state and vice-versa. This measurement principle can be gathered from, for example, the scientific publication "Detection and Size Analysis of Proteins with Switchable DNA Layers", Nano Letters, 2009, Vol. 9, 1290-1295. By causing the movement of the nucleic acid structure from the lying into the standing position, a dynamical method for detecting binding interactions is provided. This method facilitates the detection based on a change of the dynamical behaviour of the nucleic acid structure due to the binding of a binding partner to a ligand of the nucleic acid structure. These aspects of the present invention make use of the fact that the nucleic acid structure is electrically charged and thus has a polarity. In other words, in this embodiment the herein presented method makes use of the "switchSENSE™" technology as has been described before. In further embodiments of this method the detection is based on an observed change of a hydrodynamic resistance of the switched molecules. More details hereof will be explained in the context of the Examples and Figures hereinafter.

According to another exemplary embodiment of the invention quenching the signal of the label is used, wherein the quenching mechanism used depends on the distance between the quenching medium and the label. Thus, the used quenching is distant dependent (Kaiser and Rant (2010) J. Am. Chem. Soc. 132: 7935).

For example, on a biochip a quenching layer, which is used also as an electrode, may be provided to facilitate the quenching of electromagnetic radiation emission from the label. An applied bias polarizes the electrode, leading to the formation of a Gouy-Chapman-Stern screening layer. Non-radiative energy transfer from the label to surface plasmons in the quenching layer may quench the emitted signal intensity when the label approaches the surface. Therefore, high signal intensities indicate a standing configuration of the nucleic acid structure and less quenching during negative applied electrode bias. Low signal intensities indicate a lying configuration of the nucleic acid structure during positive applied electrode bias. The latter is the case for a quenching layer being close to the substrate. However, said quenching layer may also be positioned opposite of the electrode, e.g. on the counter electrode.

If the electrode is a metal, a photoluminescent (PL) label which emits low photoluminescence, even when irradiated with light of an absorbable wave length as long as it interacts with the metal, for example when positioned near the metal, but which is capable of emitting photoluminescence in response to the light energy when exposed to light at an absorbable wave length, if it does not interact with the metal, for example when positioned away from the metal, is particularly suitable for using the emitting/quenching mechanism described herein. The label may be selected according to the following aspects. The absorption spectrum of the quenching medium coincides to some extent with the emission spectrum of the label, such that non-radiative energy transfer is possible. For example, the label may be a PL emitter and can be an organic dye molecule or also a nanoparticle.

a) The immobilized single-stranded nucleic acid molecule (shown as black helix) is labelled with a fluorescent dye (grey circle) and forms a double strand with a first single-stranded nucleic acid molecule (shown as helix with white filling) and a second single-stranded nucleic acid molecule (shown as dashed helix). The ligand bound to the first single-stranded nucleic acid molecule is shown as square and the ligand bound to the second single-stranded nucleic acid molecule is shown as pentagon.

b) The immobilized single-stranded nucleic acid molecule (shown as black helix) is labelled with a fluorescent dye (grey circle) and forms a double strand with a first single-stranded nucleic acid molecule (shown as shorter black helix), a second single-stranded nucleic acid molecule (shown as helix with white filling) and a third single-stranded nucleic acid molecule (shown as dashed helix). The ligand bound to the first single-stranded nucleic acid molecule is shown as square and the ligand bound to the second single-stranded nucleic acid molecule is shown as pentagon.

Figure 2:
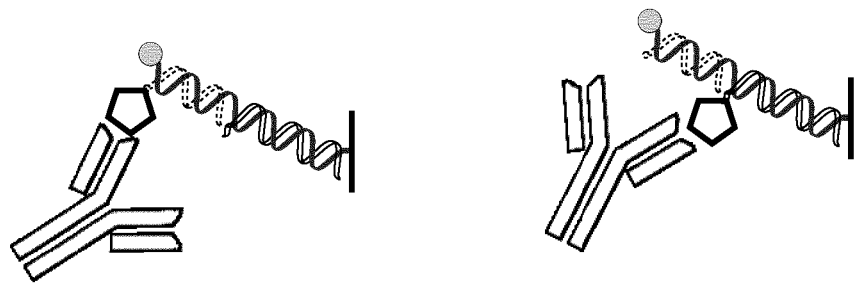
Figure 2:
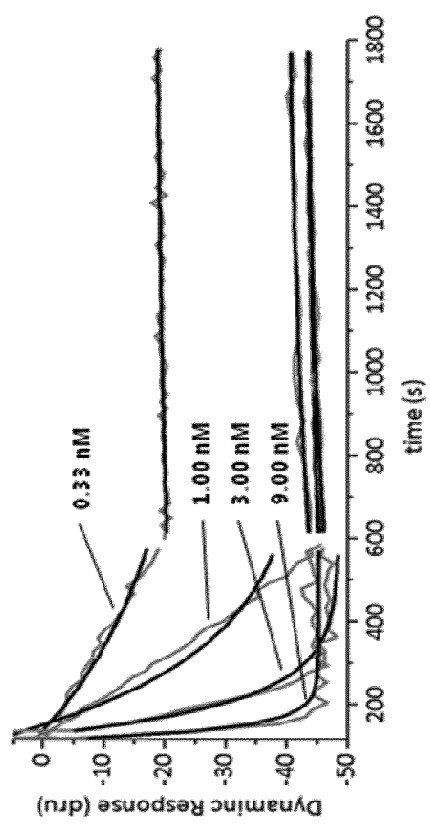
Figure 2:
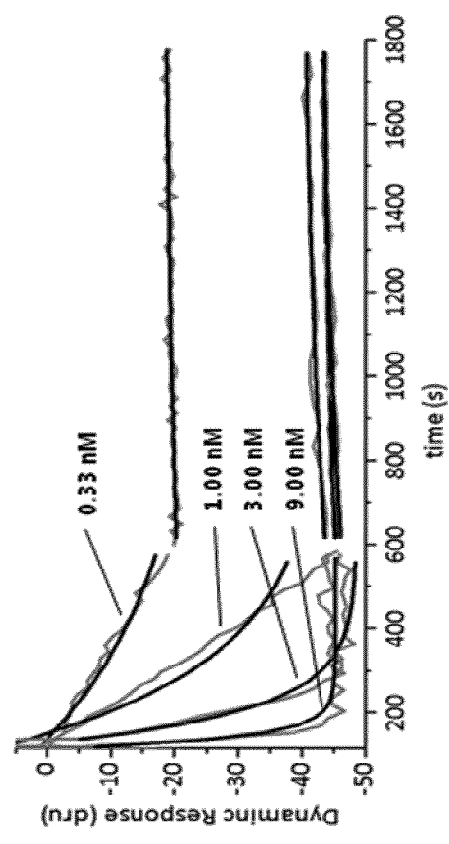
Figure 3:
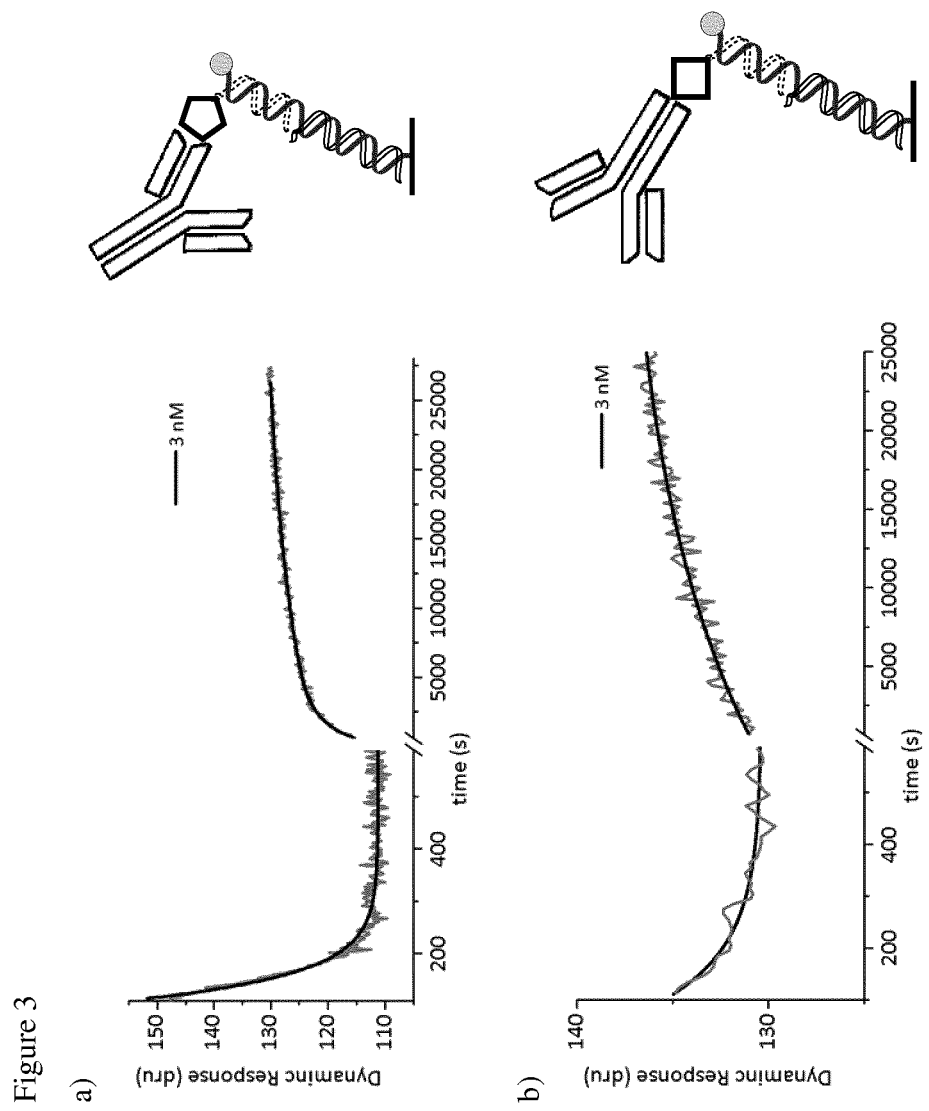

FIG. 2: Analysis of the interaction of the indicated amounts of the anti-Dig IgG1κ antibody with digoxigenin coupled either to the upper (a) or the lower (b) DNA single strand FIG. 3: Analysis of the interaction of the indicated amounts of the anti-Dig IgG1κ antibody with digoxigenin (a), protein G (b) and both digoxigenin and protein G (c)

DETAILED DESCRIPTION OF THE INVENTION

The present invention as illustratively described in the following may suitably be practiced in the absence of any element or elements, limitation or limitations, not specifically disclosed herein.

The present invention will be described with respect to particular embodiments and with reference to certain figures, but the invention is not limited thereto, but only by the claims.

Where the term "comprising" is used in the present description and claims, it does not exclude other elements. For the purposes of the present invention, the term "consisting of" is considered to be a preferred embodiment of the term "comprising". If hereinafter a group is defined to comprise at least a certain number of embodiments, this is also to be understood to disclose a group which preferably consists only of these embodiments.

Where an indefinite or definite article is used when referring to a singular noun, e.g. "a", "an" or "the", this includes a plural of that noun unless something else is specifically stated. The terms "about" or "approximately" in the context of the present invention denote an interval of accuracy that the person skilled in the art will understand to still ensure the technical effect of the feature in question. The term typically indicates deviation from the indicated numerical value of ±20%, preferably ±15%, more preferably ±10%, and even more preferably ±5%.

Furthermore, the terms "first", "second", "third" or "(a)", "(b)", "(c)", "(d)" or "(i)", "(ii)", "(iii)", "(iv)" etc. and the like in the description and in the claims are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

In case the terms "first", "second", "third" or "(a)", "(b)", "(c)", "(d)" or "(i)", "(ii)", "(iii)", "(iv)" etc. relate to steps of a method or use or assay there is no time or time interval coherence between the steps unless indicated otherwise, i.e. the steps may be carried out simultaneously or there may be time intervals of seconds, minutes, hours, days, weeks, months or even years between such steps, unless otherwise indicated in the application as set forth herein above or below.

Technical terms are used by their common sense. If a specific meaning is conveyed to certain terms, definitions of terms will be given in the following in the context of which the terms are used.

Within the meaning of the present invention a "nucleic acid structure" is a secondary structure formed by the interaction between an immobilized single-stranded nucleic acid molecule with a first and a second single-stranded nucleic acid molecule.

Figure 1:
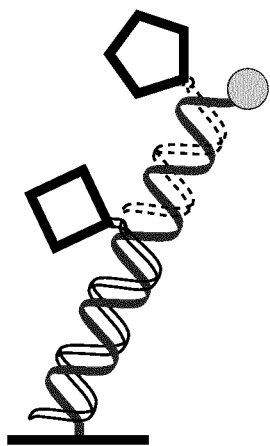
FIG. 1: Schematic drawing of two representative nucleic acid structures used in the method of the present invention.
Figure 1:
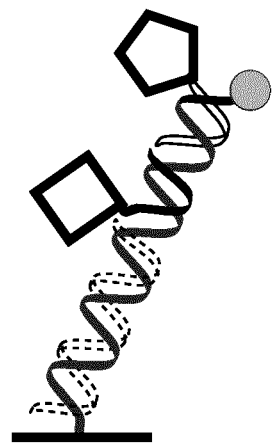

Exemplary nucleic acid structures are shown in FIG. 1.

The term "nucleic acid" refers to any type of nucleic acid molecule such as DNA or RNA or PNA or LNA with DNA being the preferred nucleic acid.

The immobilized single-stranded nucleic acid molecule forms a double strand with the first and the second single-stranded nucleic acid molecule by the interaction of complementary bases in the single strands in a process known as hybridization.

The person skilled in the art knows how to select sequences such that they form a double strand. In particular, it is well-known that a nucleotide double-strand forms by forming hydrogen bonds between complementary bases, i.e. between adenine and thymine or between cytosine and guanine.

Hence, the immobilized single-stranded nucleic acid molecule has to contain a first sequence which is complementary to the sequence of the first single-stranded nucleic acid molecule and a second sequence which is complementary to the sequence of the second single-stranded nucleic acid molecule. It is apparent that the first and second sequences have to be sufficiently different from each other to avoid a cross-hybridization, i.e. a hybridization of the second single-stranded nucleic acid molecule with the first sequence of the immobilized single-stranded nucleic acid molecule and/or a hybridization of the first single-stranded nucleic acid molecule with the second sequence of the immobilized single-stranded nucleic acid molecule. Hence, the first and the second single-stranded nucleic acid molecules bind to separate, non-overlapping parts of the immobilized nucleic acid molecule.

The first and the second single-stranded nucleic acid molecule may together bind over the whole length of the immobilized single-stranded nucleic acid molecule. Alternatively, the first and the second single-stranded nucleic acid molecule may not together bind over the whole length of the immobilized single-stranded nucleic acid molecule and a third single-stranded nucleic acid molecule may bind to the immobilized single-stranded nucleic acid molecule at a sequence which is not bound by any of the first and the second single-stranded nucleic acid molecules. The third single-stranded nucleic acid molecule may bind between the first and the second single-stranded nucleic acid molecule, if the first and the second single-stranded nucleic acid molecule do not bind adjacent to each other, or it may bind between the site of immobilization and the first single-stranded nucleic acid molecule.

Preferably, the immobilized single-stranded nucleic acid molecule does not contain repetitive sequences. The term "repetitive sequences" denotes two or more identical or substantially identical sequences within a single-stranded nucleic acid molecule wherein each repetitive sequence within the single-stranded nucleic acid molecule forms a double strand with one single-stranded nucleic acid molecule having a specific sequence which is complementary or substantially complementary to the repetitive sequence. Hence, at least two single-stranded nucleic acid molecules of the same sequence hybridize to the single-stranded nucleic acid molecule containing at least two repetitive sequences. The skilled person knows that the repetitive sequence has to have a certain length so that a double strand can form between the part of the single-stranded nucleic acid molecule comprising the repetitive sequence and the single-stranded nucleic acid molecule having the complementary sequence. The minimum length for the repetitive sequence is therefore four nucleotides.

Accordingly, the immobilized single-stranded nucleic acid molecule does not contain repetitive sequences with a length of at least four nucleotides.

The first and the second single-stranded nucleic acid molecule may bind adjacent to each other. Alternatively, a part of the immobilized single-stranded nucleic acid molecule may not be bound by any of the single-stranded nucleic acid molecules to form a double strand, but may remain single-stranded. Preferably, the length of this part not forming a double strand is not more than 3 nucleotides, more preferably it is not more than 2 nucleotides, even more preferably it is not more than 1 nucleotide and most preferably the first and the second single-stranded nucleic acid molecules bind adjacent to each other.

If only one single-stranded nucleic acid molecule to which two ligands are attached is used to form a double strand with the immobilized single-stranded nucleic acid molecule, the immobilized single-stranded nucleic acid molecule has to contain a sequence which is complementary to the sequence of this single-stranded nucleic acid molecule. The single-stranded nucleic acid molecule to which two ligands are attached may bind over the whole length of the immobilized single-stranded nucleic acid molecule so that one ligand is located close to the solid substrate. Alternatively, the single-stranded nucleic acid molecule to which two ligands are attached may not bind over the whole length of the immobilized single-stranded nucleic acid molecule. In this case, a further single-stranded nucleic acid molecule to which no ligand is attached may bind to the immobilized single-stranded nucleic acid molecule at a sequence which is not bound by the single-stranded nucleic acid molecule to which two ligands are attached.

The double strand between the immobilized single-stranded nucleic acid molecule and the first and the second single-stranded nucleic acid molecules or the single-stranded nucleic acid molecule to which two ligands are attached forms, if the sequences are contacted under suitable conditions, i.e. a pH above 2, a salt concentration equivalent to more than 20 mM NaCl and a temperature below the melting temperature of the double strand which is dependent on the length of the double strand. Suitable conditions for forming a double strand are also known to the skilled person and include the use of a buffer comprising 40 mM NaCl, 10 mM sodium phosphate buffer, pH 7.4 and 0.05% Tween 20 at a temperature of 25° C.

The sequences forming the double strand do not have to be 100% complementary to each other, meaning that in the double strand one or more bases may not be paired with their complementary base. The person skilled in the art knows that longer double-stranded molecules permit a larger number of non-pairing bases than shorter double-stranded molecules without significantly influencing the stability of the double strand. In general, at least 50%, preferably at least 60% and more preferably at least 70% of the bases within the sequences forming the double strand should be complementary to each other.

In the method of the present invention preferably all nucleotides of the first and the second single-stranded nucleic acid molecule or the single-stranded nucleic acid molecule to which two ligands are attached take part in the formation of the double strand with the immobilized single-stranded nucleic acid molecule, i.e. the first and the second single-stranded nucleic acid molecule or the single-stranded nucleic acid molecule to which two ligands are attached do not contain any nucleotides which do not form part of the double-strand with the immobilized single-stranded nucleic acid molecule. In particular, the first and the second single-stranded nucleic acid molecule or the single-stranded nucleic acid molecule to which two ligands are attached do not contain any linker between the part of the nucleic acid molecule which forms a double strand with the immobilized single-stranded nucleic acid molecule and the part of the nucleic acid molecule to which the ligand is attached.

The sequence of the single-stranded nucleic acid molecules has to be selected such that it does not comprise self-complementary sequences, meaning that substantially no double strands, for example no double strands with a length of more than four basepairs, are formed between sequences within the single-stranded nucleic acid molecules. Further, the sequences of the first and the second single-stranded nucleic acid molecule have to be selected such that substantially no double strand, i.e. a double strand with a length of more than four basepairs, is formed between the first and the second nucleic acid molecule.

For immobilizing the immobilized single-stranded nucleic acid molecule to a substrate, said nucleic acid molecule may be attached to a linker which facilitates the attachment to the surface. Suitable linker molecules are known to the skilled person and depend on the surface to which the nucleic acid structure is to be attached. If the substrate is a gold surface, the linker is preferably a thiol linker such as $(CH_2)_6$—SH or di-thiol phosphoramidite. For glass or silicium surfaces a silane linker may be used. If the surface is modified with avidin, the linker may be biotin. An overview of further linkers is provided on the website of the company Integrated DNA Technologies (IDT). Methods for attaching a linker to a nucleic acid molecule are well-known and include the use of thiolated nucleotides (see Hegner et al. (1993) FEBS 336(3): 452-456). Nucleic acid molecules with an attached linker can be obtained commercially from companies such as Eurofins Genomics or atdbio.

Within the present invention the single-stranded nucleic acid molecule forming a double strand with the first and the second nucleic acid molecules or the single-stranded nucleic acid molecule to which two ligands are attached does not have to be immobilized directly to the substrate, but can also be immobilized via one or more helper nucleic acid molecules which are themselves immobilized to the substrate with one end of the helper molecule, while the other end of the helper nucleic acid molecule hybridizes with the single-stranded nucleic acid molecule to be immobilized over a part of this single-stranded nucleic acid molecule which does not take part in the formation of the double strand with the first and the second single-stranded nucleic acid molecules. It is apparent that the part of the single-stranded nucleic acid molecule which hybridizes with the helper nucleic acid molecule(s) cannot be the same as the part which forms a double strand with the first and the second nucleic acid molecules or with the single-stranded nucleic acid molecule to which two ligands are attached.

In the terminology used in the present application the first single-stranded nucleic acid molecule is the nucleic acid molecule which hybridizes to a sequence of the immobilized single-stranded nucleic acid molecule which is located closer to the site of immobilization than the sequence to which the second single-stranded nucleic acid molecule hybridizes. Typically, but not necessarily, the ligand is attached to the first single-stranded nucleic acid molecule at the end of the first single-stranded nucleic acid molecule which is more distal from the site of immobilization than the other end.

The second single-stranded nucleic acid molecule within the meaning of the present invention is the nucleic acid molecule which hybridizes to a sequence of the immobilized single-stranded nucleic acid molecule which is more distal from the site of immobilization than the sequence to which the first single-stranded nucleic acid molecule hybridizes. Typically, but not necessarily, the ligand is attached to the second single-stranded nucleic acid molecule at the end of the second single-stranded nucleic acid molecule which is more distal from the first single-stranded nucleic acid molecule than the other end.

The first and second single-stranded nucleic acid molecules can be hybridized to the immobilized single-stranded nucleic acid molecule together, so that the hybridization reaction comprises the first and second single-stranded nucleic acid molecules and the immobilized single-stranded nucleic acid molecule. Alternatively, the first and second single-stranded nucleic acid molecules can be hybridized to the immobilized single-stranded nucleic acid molecule sequentially, meaning that in a first step the first or second single-stranded nucleic acid molecule is hybridized to the immobilized single-stranded nucleic acid molecule, before in a second step the second or first, respectively, single-stranded nucleic acid molecule is added or hybridized in a separate hybridization reaction.

A nucleic acid structure in which the first and second single-stranded nucleic acid molecules are hybridized to the immobilized single-stranded nucleic acid molecule is illustrated in FIG. 1a.

In one embodiment, the first and second single-stranded nucleic acid molecules may not hybridize over the whole length of the immobilized single-stranded nucleic acid molecule. Instead, at least a third single-stranded nucleic acid molecule may also hybridize to a part of the immobilized single-stranded nucleic acid molecule to which the first and the second single-stranded nucleic acid molecules do not hybridize, preferably in the region of the immobilized single-stranded nucleic acid molecule which is closest to the site of immobilization. Such a nucleic acid structure is illustrated in FIG. 1b.

The first and second single-stranded nucleic acid molecules may have the same or a different length. If they have a different length, they should be able to form a stable double strand with the immobilized single-stranded nucleic acid molecule under the same conditions.

The first and the second single-stranded nucleic acid molecule or the single-stranded nucleic acid molecule to which two ligands are attached may each have a length of 7 to 300 nucleotides, preferably of 10 to 250, more preferably of 20 to 200, even more preferably of 20 to 150 and most preferably of 20 to 100 nucleotides. If the length of the first and/or the second nucleic acid molecule is below 10 nucleotides, the nucleic acid molecule is preferably PNA (peptide nucleic acid) which consists of a backbone having repeating N-(2-aminoethyl)-glycine units linked by peptide bonds to which the various purine and pyrimidine bases are linked by a methylene bridge (—$CH_2$-) and a carbonyl group (—(C=O)—). In one particular embodiment the first single-stranded nucleic acid molecule has a length of 28 nucleotides and the second single-stranded nucleic acid molecule has a length of 20 nucleotides.

If the first and second single-stranded nucleic acid molecules hybridize over the whole length of the immobilized single-stranded nucleic acid molecule, the length of the immobilized single-stranded nucleic acid molecule corresponds to the sum of the lengths of the first and second single-stranded nucleic acid molecules. If the first and second single-stranded nucleic acid molecules do not hybridize over the whole length of the immobilized single-stranded nucleic acid molecule, the length of the immobilized single-stranded nucleic acid molecule is larger than the sum of the lengths of the first and second single-stranded nucleic acid molecules.

If the first and second single-stranded nucleic acid molecules hybridize over the whole length of the immobilized single-stranded nucleic acid molecule, the distance between the ligands attached to the first and second single-stranded nucleic acid molecules is determined by the length of the second single-stranded nucleic acid molecule (see also FIG. 1a).

If at least a third single-stranded nucleic acid molecule hybridizes to the immobilized single-stranded nucleic acid molecule at a sequence close to the site of immobilization, the ligand may also be attached to the end of the first single-stranded nucleic acid molecule which is closer to the site of immobilization so that in this case the distance between the ligands is determined by the sum of the lengths of the first and second single-stranded nucleic acid molecules (see also FIG. 1b).

If the first ligand is attached to a first end and the second ligand is attached to a second end of the same single-stranded nucleic acid molecule (which is then called the "single-stranded nucleic acid molecule to which two ligands are attached"), the distance between the ligands is the length of the single-stranded nucleic acid molecule.

Preferably, the distance between the ligands is selected such that the ligands are located at the same side of the double strand formed between the immobilized single-stranded nucleic acid molecule and the first and second single-stranded nucleic acid molecule or the single-stranded nucleic acid molecule to which two ligands are attached. Since one turn of the nucleic acid double helix corresponds to about ten basepairs, the distance should preferably be an integer of 10 nucleotides, such as 10 nucleotides, 20 nucleotides or 30 nucleotides, etc.

The double strand formed between the immobilized single-stranded nucleic acid molecule and the at least first and second single-stranded nucleic acid molecule or the single-stranded nucleic acid molecule to which two ligands are attached may consist of DNA, RNA, PNA and LNA homoduplexes and heteroduplexes thereof such as DNA/RNA, DNA/PNA, DNA/LNA, RNA/PNA and PNA/LNA. As already discussed above, the kind of nucleic acid used may influence the stability of the double strand so that the minimal length required for the formation of a stable double strand depends on the type of nucleic acid forming the double strand.

The person skilled in the art is aware of methods for attaching ligands such as proteins to nucleic acid molecules. One possibility is to modify the nucleic acid molecule by 6-maleimidohexanoic acid N-hydroxysuccinimide ester and then to react the modified DNA with the protein having suitable amino acid residues for conjugation (see, e.g., Fujiwara et al. (1988). J. Immunol. Methods 112: 77-83; Peeters et al. (1989). J. Immunol. Methods 120: 133-143). Further, kits are available for producing protein-nucleic acid conjugates, for example from Solulink. An overview of different conjugation techniques is provided in Hermanson, Bioconjugate Techniques, Elsevier, third edition 2013 and in Mark, Bioconjugation Protocols, Humana Press, second edition 2011.

Within the method of the present invention a "ligand" is a molecule which can bind to another molecule by non-covalent bonds due to a specific affinity to the other molecule. The ligand has a chemical structure which is different from that of the nucleic acid molecule to which it is attached meaning that the ligand is not a nucleic acid molecule.

Within the meaning of the present invention the term "ligand" is intended to include, but not being limited to, proteins or parts thereof as well as non-proteinaceous chemical molecules which have to have a size which does not interfere with the formation of the double strand, i.e. so-called small molecules.

The term "small molecule" is intended to include organic molecules with a molecular weight of less than 500 Dalton and a size in the nanomolar range. The term "small molecule" is not intended to include electrochemically active compounds such as methylene blue and different ions. "Electrochemically active compound" means any substance which has the proper reduction potential to receive electrons at the active site. In particular, the term "small molecule" does not include methylene blue.

Preferably, the ligand is an antigen and more preferably the ligand is a protein or part thereof. Also preferably, the ligand is not an antibody. The part of the protein may have a minimum length of at least six amino acids which is the minimum length of an epitope which is recognized by an antibody.

An antigen is any structural substance which is recognized by an antibody and includes, but is not limited to, peptide antigens, lipid antigens and carbohydrate antigens.

The first and the second ligand attached to the single-stranded nucleic acid molecule may be the same, i.e. they may have the same chemical structure. For example, if the interaction of a bivalent, monospecific full-length antibody with an antigen is to be analyzed, the first and the second ligand may be said antigen.

In an alternative embodiment, the first and the second ligand attached to the single-stranded nucleic acid molecule may be different, i.e. they may have a different chemical structure. In the case of proteins, different proteins or parts of different proteins may be used as first and second ligand. For example, if the interaction of a bispecific antibody with its target antigens is to be analyzed, the first ligand may be the first antigen or part thereof and the second ligand may be the second antigen or part thereof, wherein the first and the second antigens are the target antigens of the bispecific antibody. Alternatively, different parts of the same protein may be used as first and second ligand which for example allows determining the binding epitope of an antibody. In a further alternative, the first and the second ligand may have the same amino acid sequence, but may differ in post-translational modifications such as phosphorylations, methylations and acetylations. This embodiment allows the analysis of the influence of post-translational modifications on the binding of a binding partner such as the binding of an antibody to its target antigen.

The first ligand may also be a small molecule and the second ligand may be a protein or part thereof or vice versa. Such an embodiment may be used to investigate the allosteric inhibition of an enzyme which is the binding partner by a small molecule. If the binding partner to be analyzed with the method of the present invention is a signal transduction molecule, the first ligand may be a protein which is supposed to be upstream of the binding partner in the signal transduction cascade and the second ligand may be a protein which is supposed to be downstream of the binding partner in the signal transduction cascade.

Preferably, the first and the second nucleic acid molecule or the single-stranded nucleic acid molecule to which a first and a second ligand are attached are not labelled with a detectable level such as a fluorescent dye.

In the method of the present invention either (a) the nucleic acid structure or (b) the first and the second single-stranded nucleic acid molecule or (c) the single-stranded nucleic acid molecule to which a first and a second ligand is attached is contacted with a sample of the binding partner which is to be analyzed so that the ligand and the binding partner can interact, i.e. under conditions which allow the ligand and the binding partner to interact. Suitable conditions involve the use of a suitable buffer such as a buffer comprising sodium chloride and a buffer, preferably a buffer comprising sodium chloride and a phosphate buffer and more preferably a buffer comprising 40 mM NaCl, 10 mM sodium phosphate buffer, pH 7.4 and 0.05% Tween.

The nucleic acid structure is attached to a substrate. The term "substrate" is to be understood in its broadest sense as a structure to which a nucleic acid molecule can be coupled reversibly or irreversibly and includes, for example, planar matrices such as chips or beads. The substrate may be made of any substance, like e.g. glass, to which a nucleic acid molecule can be attached and may be made, e.g. from gold or other metals. For switching applications as described herein, a biochip may be used which comprises a film on top of said substrate. For example, a gold film of 5-300 nm thickness may be used on a glass substrate or an organic layer, e.g. a conducting polymer or a dye-sensitized matrix may be used on the substrate. This layer may function as a quenching layer used in an embodiment of the detection method.

As discussed above, to attach a nucleic acid molecule to a substrate a linker molecule such as a thiol may be required which is attached to the nucleic acid structure and enables the binding of the nucleic acid structure to the substrate by a chemical reaction. According to another exemplary embodiment of the invention the chemical linker is chosen from the group that contains one of—or a combination of—the following reactive groups: aldehyde, ketone, thiol, amine, carboxyl, hydrazine, hydrazide, hydroxyl, glycan, azide, alkyne, alkene, silicon, and any combination thereof.

In a preferred embodiment of the present invention the substrate is a gold surface to which the nucleic acid structure is coupled by means of a thiol linker which is attached to the immobilized single-stranded nucleic acid molecule.

In the method of the present invention a substrate is used to which at least one nucleic acid structure is attached via the immobilized single-stranded nucleic acid molecule. Alternatively, two, three, four, five, six, seven, eight, nine or ten, 12, 14, 16, 18, 20, 22, 24, 26, 28 or 30 different nucleic acid structures may be attached to the substrate. Preferably, six different nucleic acid structures are attached to one substrate. Also preferably, the different nucleic acid structures attached to the same substrate differ in the sequence of the immobilized single-stranded nucleic acid molecule and of the first and second single-stranded nucleic acid molecules. Further, after analyzing one or more interactions on a substrate with a pair of first and second single-stranded nucleic acid molecules attached to one or more specific ligands, the substrate with the immobilized single-stranded nucleic acid molecule attached to it can be used for the analysis of further interactions after removing the first and second single-stranded nucleic acid molecules or the single-stranded nucleic acid molecule to which two ligands are attached from the immobilized single-stranded nucleic acid molecule. The single-stranded nucleic acid molecules can for example be removed by treatment with a strongly basic solution such as a solution with pH 13 which denatures the double strand between the immobilized single-stranded nucleic acid molecule and the single-stranded nucleic acid molecules. After removing the first and second single-stranded nucleic acid molecules or the single-stranded nucleic acid molecule to which two ligands are attached from the immobilized single-stranded nucleic acid molecule, the immobilized single-stranded nucleic acid molecule can be hybridized with first and second single-stranded nucleic acid molecules or single-stranded nucleic acid molecules to which two ligands are attached having other ligands attached to them. It could be shown that the substrate can be re-used at least 16 times without significantly influencing the quality of the analysis.

If the method of the present invention is to be used for example with the "Switchsense" technology, the nucleic acid structure may be labeled with a fluorescent dye. Suitable fluorescent dyes are known to the skilled person and include FITC, fluoresceine, rhodamine green, rhodamine red, cyanine3 and cyanine5. Preferably, cyanine 3 and/or cyanine5 are used. Nucleic acid molecules which are labeled with fluorescent dyes can be obtained from different suppliers such as Eurofins Genomics or Genscript. Within the nucleic acid structure the fluorescent dye is located in the immobilized single-stranded nucleic acid molecule and it is located at the terminus of the immobilized single-stranded nucleic acid molecule which is not used for immobilization and is therefore available for labelling.

If the method of the present invention is to be used with surface plasmon resonance or bio-layer interferometry as described in the introductory portion, the method further comprises the steps of:

d) applying light to the surface;
e) measuring the intensity, angle, or spectrum of the reflected light; and
f) detecting an interaction of the binding partner with the first and the second ligand by observing a signal change in the intensity, angle, or spectrum of the reflected light.

The method of the present invention is used to detect and/or analyze interactions between molecules, in particular the interaction of one or more antigens with an antibody. The term "detecting" means that it can be determined whether such an interaction indeed exists or not. The characterization of a known interaction includes the determination of parameters such as affinity and/or avidity of the molecules to each other, the binding kinetics, i.e. the kinetics of association and dissociation between two molecules, the size of the molecules, conformational changes in the three-dimensional structure of the molecules, chemical modifications changes in the charge of the molecules, binding energies (free energy, enthalpy, entropy) in equilibrium, energy barriers involved in association or dissociation processes and the like.

The present invention is described with particular reference to the analysis of antigen/antibody interactions by the so-called "switchSENSE" technology. However, it becomes apparent from the present description that the present invention can also be used to detect and/or analyze interactions of other molecules by other detection techniques such as surface plasmon resonance.

EXAMPLES

1. Biochip

The biochip consists of a glass substrate (27×40 mm) with eight holes (1 mm diameter) which serve as in- and outlets for four flow channels. Au work electrodes (120 µm diameter) and Pt counter electrodes were arranged in 4 areas with 6 electrodes each and fabricated by standard optical lithography and metallization techniques. Prior to DNA immobilization, the surface was cleaned in freshly prepared Piranha solution (95% $H_2SO_4$:30% $H_2O_2$=2:1) for 15 minutes, followed by extensive rinsing with deionized water, 3 min sonication and drying with nitrogen.

2. Preparation of DNA Layers of the Present Invention (Also Called "Bispecific Nanolevers")

Thiolated 48mer oligonucleotides were end-grafted to the gold electrodes via spotting with a pico-liter dispensing system in immobilization buffer (10 mM Tris pH 7.4, 200 mM NaCl, 1 µM DNA). The sequence of the Cy3 labelled ss-DNA for immobilization was 5'HS—$(CH_2)_6$-TAG TCG TAA GCT GAT ATG GCT GAT TAG TCG GAA GCA TCG AAC GCT GAT-Cy3 3' (SEQ ID NO: 3) (Metabion, Germany). After a 10 min incubation, the chip was assembled by using double adhesive film with die-cut flow channels as an intermediate layer and a cover slide as a top layer. The flow channels were 60 µm high and 1 mm wide and covered one of four electrode areas each. The DNA-modified Au electrodes were passivated and unspecifically bound DNA was removed by co-adsorbing mercaptohexanol (1 mM in 'T'-buffer: 10 mM Tris pH 7.4, 50 mM NaCl) for 30 min.

After installation in the setup, the DNA layers were hybridized with the two complementary DNAs c7-20-5'ligand (the second single-stranded nucleic acid molecule) and c7-28-5'ligand (the first single-stranded nucleic acid molecule) in P40 buffer (40 mM NaCl, 10 mM sodium phosphate buffer, pH 7.4 and 0.05% Tween) and the density was adjusted using a previously reported electrical desorption procedure.

The DNA of c7-20-5'ligand has the following sequence: ATC AGC GTT CGA TGC TTC CG and is modified at the 5'end with antigen 1-HS—$(CH_2)_6$— (SEQ ID NO: 2).

The DNA of c7-28-5'ligand has the following sequence: A CTA ATC AGC CAT ATC AGC TTA CGA CTA (SEQ ID NO:1) and is modified at the 5'end with antigen 2-HS—(CH2)6-.

Briefly, the relative switching amplitude ΔF/F (ΔF is the observable fluorescence modulation amplitude when applying repulsive or attractive potentials, and F is fluorescence at repulsive potential) is used as a parameter that indicates the free mobility of DNA strands on the surface. Due to steric interactions, densely packed DNA levers cannot lie down on the surface, i.e. cannot be switched (ΔF/F≈0%), while ultra-low-density layers feature ΔF/F values close to 100%. By applying negative voltage pulses (e.g. −0.8V vs. Pt) for a couple of seconds, DNA was electrically desorbed from the surface until ΔF/F became maximal, indicating free DNA movement in a very dilute layer (density estimation <$10^{10}$ molecules/cm$^2$).

If required, double stranded DNA layers were denatured by rinsing 25 µl NaOH solution (pH 12-13) over the electrodes for 10 s. The layers could then be regenerated by hybridization with fresh complementary DNA (100 nM in 25 µl buffer). A flow rate of 100 µl/min was typically used during sensing experiments, which was high enough to operate the sensor in the reaction-limited kinetics regime. An effect of the applied hydrodynamic flow on the DNA switching behaviour was not observed.

3. Measurement Setup

Biosensing measurements were performed with the DRX 2400 switchSENSE analyser instrument from Dynamic Biosensors GmbH. Fluorescent light from the Cy3-labeled DNA nucleic acid structures was excited by a green LED (517 nm bandpass filtered) that was coupled into a 50× objective via a dichroic mirror. Emitted Cy3 fluorescence light (570 nm) was collected by the same objective, passed through the dichroic mirror and a long pass filter, and detected with a photomultiplier (Hamamatsu). AC square-wave signals from a frequency generator were used to actuate the DNA molecules and simultaneously trigger an event timer of a single photon counting unit (NanoHarp, PicoQuant, Germany) to record the photon arrival time with 32 ns resolution. A Peltier element integrated in the sample holder enabled temperature controlled experiments.

Before every time-resolved (TR) fluorescence measurement, the static fluorescence response to an applied voltage ramp was recorded. The switching potentials for TR measurements were chosen to be close to the two 'plateau regions' of the fluorescence response (indicating completely lying and completely standing DNA). The voltage amplitude was between 0.6 V and 1 V, the DC offset (≈4.0 V) was adjusted (app. ±0.1 V) according to the "potential of conformation transition", i.e., the inflection point in the measured voltage response curve. The frequency of the applied square wave potential was 10 kHz, which ensured that the DNA had enough time to stand up and lie down completely before reversing the voltage.

The Dynamic Response is calculated from the normalized fluorescence signal $F_{norm}$ as $$DR_{t1_{up}}{}^{t2}=\int_{t1}^{t2}F_{norm}dt, DR_{t1_{down}}{}^{t2}=\int_{t1}^{t2}(1-F_{norm})dt,$$

for the upward and the downward motions, respectively.

For the analysis of an antibody with its antigen(s) 450 μL antibody solution (dissolved in P40 buffer (40 mM NaCl, 10 mM sodium phosphate buffer, pH 7.4 and 0.05% Tween)) at different concentrations (0.33, 1, 3, 9, 27 nM) was injected with a flow rate of 50 μL/min. The interaction with a ligand molecule was analyzed in a time-resolved measurement. After saturation of the ligand layer by the antibody the dissociation over several hours was measured.

In a further step the kinetic data set is uploaded into switch ANALYSIS software (Dynamic Biosensors GmbH, DE). It provides information for the calculation of the $k_{on}$, $k_{off}$ and $K_d$. The fraction of target molecules, which are bound by ligands at a given time, is evaluated from the Dynamic Response (DR) or the fluorescence modulation amplitude. For the evaluation of the association and dissociation constant, the raw data has to be fitted by the following exponential function:

$$f(t) = A_0 + A_1 \exp(-(t-t_0)/\tau)$$

The end or saturation level is described as $A_0$ while $A_1$ reflects the amplitude between start and end level. The time t has to be adjusted by the time offset $t_0$. The time constant of the exponential function is $\tau$. The observable association and dissociation time constant $\tau_{on}$ and $\tau_{off}$ can be used to calculate $k_{on}$, $k_{off}$ and $K_d$.

4. Analysis of Bispecific Antibody Binding

The binding of an antibody recognizing digoxigenin (dig) by its antigen-binding site and further binding protein G by its constant Fc region was analyzed in the setup described above.

In a first experiment it was investigated whether the binding kinetics of the antibody to digoxigenin (anti-Dig IgG1 κ) is influenced by the site of ligand coupling, i.e. by coupling the ligand to the lower and the upper strand. To this end, digoxigenin was coupled to either the upper c-20 strand (the second single-stranded nucleic acid molecule within the terminology of the present application) or the lower c-28 strand (the first single-stranded nucleic acid molecule within the terminology of the present application).

The results of this analysis are shown in FIGS. 2a and 2b and the $k_{on}$, $k_{off}$ and $K_d$ values calculated from this analysis are presented in Table 1:

| antiDig vs Dig | | $k_{on,1}$ (E + 6 M$^{-1}$s$^{-1}$) | $k_{off,1}$ (E − 4 s$^{-1}$) | $K_{d,1}$ (pM) |
|---|---|---|---|---|
| anti-Dig | c20-Dig | 3.9 ± 0.3 | 10.6 ± 4.3 | 268 ± 111 |
| IgG1 κ | c28-Dig | 3.4 ± 0.3 | 10.0 ± 8.3 | 292 ± 243 |

It is apparent that the antibody binds with similar kinetics independent of the coupling of the ligand to the lower or the upper single-stranded nucleic acid molecule.

Figure 3C:
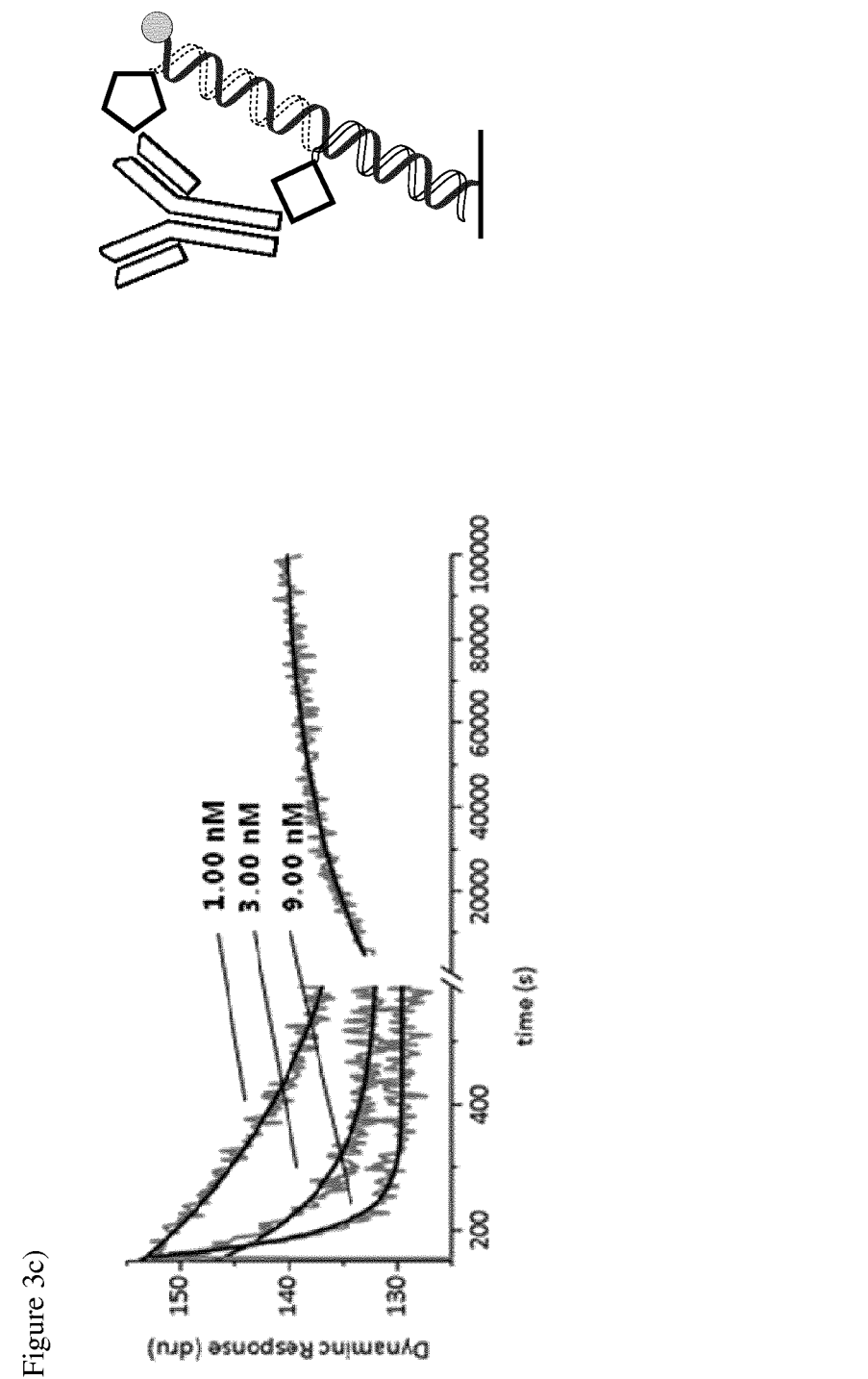

In the next set of experiments, the interaction of an anti-Dig IgG1κ antibody with digoxigenin, protein G and both digoxigenin and protein G was analyzed. The results of these analyses are shown in FIGS. 3a to c.

As expected, the interaction of the anti-Dig IgG1κ antibody with digoxigenin shows a fast off-rate and the interaction of the constant Fc-region with Protein G also results in a monophasic, fast dissociation. Finally, the bispecific interaction shows a monophasic, slow dissociation behavior. The slow dissociation behavior confirms that the antibody is in fact bound by both ligands at the same time, which results in a stronger binding. The fact that the observed dissociation kinetics are monophasic (i.e. described by a single-exponential curve) indicates that only one type of interaction, namely the conjoint (bispecific) binding of the antibody via digoxigenin and protein G is present on the surface. This confirms that both ligands are accessible to the antibody when they are immobilized on the described bispecific nucleic acid structure and that they are presented in a well-defined manner, i.e. defined distance from each other.

The invention claimed is:

1. A method for detecting and/or characterizing molecular interactions between a ligand and its binding partner, the method comprising steps a) to c) in the following order:
   a) providing a nucleic acid structure comprising
      (i) a single-stranded nucleic acid molecule which is immobilized on a solid substrate and which does not contain repetitive sequences; and
      (ii) at least a first and a second single-stranded nucleic acid molecule each of which is hybridized to a part of the immobilized single-stranded nucleic acid molecule, wherein a first ligand is attached to the first single-stranded nucleic acid molecule and a second ligand is attached to the second single-stranded nucleic acid molecule; or
         at least one single-stranded nucleic acid molecule which is hybridized to at least a part of the immobilized single-stranded nucleic acid molecule and to which a first and a second ligand are attached at different locations;
   b) contacting the nucleic acid structure with a sample of the binding partner which is to be analyzed; and
   c) detecting and/or characterizing the molecular interaction between the first and second ligands and the binding partner.

2. The method of claim 1, wherein the first ligand and the second ligand are the same.

3. The method of claim 1, wherein the first ligand is different from the second ligand.

4. The method of claim 1, wherein the first ligand and the second ligand are antigens and the binding partner is an antibody specific for said antigens.

5. The method of claim 4, wherein the antigen attached to the first single-stranded nucleic acid molecule is different from the antigen attached to the second single-stranded nucleic acid molecule and the antibody is a bispecific antibody.

6. The method of claim 1, wherein the first ligand and/or the second ligand are a protein or a part thereof, or a small molecule.

7. The method of claim 1, wherein the immobilized single-stranded nucleic acid molecule is labeled with a fluorescent dye.

8. The method of claim 1, wherein the solid substrate has at least one electrode, the immobilized single-stranded nucleic acid molecule is labeled with a fluorescent dye, and the molecular interaction is detected and/or characterized by the steps of:
   a) applying an external electrical field to the electrode to cause a movement of said combination product;
   b) observing a signal of the label during said movement of the double strand; and
   c) using the observed signal for detecting an interaction of the binding partner with the first and second ligand.

9. The method of claim 1, wherein the solid substrate has a surface from which light is reflected and the molecular interaction is detected and/or characterized by the steps of:

a) applying light to the surface;
   b) measuring the intensity, angle, or spectrum of the reflected light; and
   c) detecting an interaction of the binding partner with the first and the second ligand by observing a signal change in the intensity, angle, or spectrum of the reflected light.

10. A method for detecting and/or characterizing molecular interactions between an antibody and its cognate antigen(s), the method comprising steps a) to c) in the following order:
    a) providing a nucleic acid structure comprising
       (i) a single-stranded nucleic acid molecule which is immobilized on a solid substrate and which does not contain repetitive sequences; and
       (ii) at least a first and a second single-stranded nucleic acid molecule each of which is hybridized to a part of the immobilized single-stranded nucleic acid molecule, wherein a first antigen is attached to the first single-stranded nucleic acid molecule and a second antigen is attached to the second single-stranded nucleic acid molecule; or
          at least one single-stranded nucleic acid molecule which is hybridized to at least a part of the immobilized single-stranded nucleic acid molecule and to which a first and a second antigen are attached at different locations;
    b) contacting the nucleic acid structure with a sample of the antibody which is to be analyzed; and
    c) detecting and/or characterizing the molecular interaction between the antigen(s) and the antibody.

11. The method of claim 10, wherein the solid substrate has at least one electrode, the immobilized single-stranded nucleic acid molecule is labeled with a fluorescent dye, and the molecular interaction is detected and/or characterized by the steps of:
    a) applying an external electrical field to the electrode to cause a movement of said combination product;
    b) observing a signal of the label during said movement of the double strand; and
    c) using the observed signal for detecting an interaction of the antibody with the first and the second antigen.

12. The method of claim 10, wherein the solid substrate has a surface from which light is reflected and the molecular interaction is detected and/or characterized by the steps of:
    a) applying light to the surface;
    b) measuring the intensity, angle, or spectrum of the reflected light; and
    c) detecting an interaction of the antibody with the first and the second antigen by observing a signal change in the intensity, angle, or spectrum of the reflected light.

13. The method of claim 10, wherein the first antigen is different from the second antigen and the antibody is a bispecific antibody.

14. The method of claim 10, wherein the first and/or second antigen is a protein or a part thereof, or a small molecule.

* * * * *

SEQUENCE LISTING

<160> NUMBER OF SEQ ID NOS: 3

<210> SEQ ID NO 1
<211> LENGTH: 28
<212> TYPE: DNA
<213> ORGANISM: artificial
<220> FEATURE:
<223> OTHER INFORMATION: c7-28-5' ligand

<400> SEQUENCE: 1
actaatcagc catatcagct tacgacta                                        28

<210> SEQ ID NO 2
<211> LENGTH: 20
<212> TYPE: DNA
<213> ORGANISM: artificial
<220> FEATURE:
<223> OTHER INFORMATION: c7-20-5' ligand

<400> SEQUENCE: 2
atcagcgttc gatgcttccg                                                 20

<210> SEQ ID NO 3
<211> LENGTH: 48
<212> TYPE: DNA
<213> ORGANISM: artificial
<220> FEATURE:

```
<223> OTHER INFORMATION: single-stranded DNA for immobilization

<400> SEQUENCE: 3
tagtcgtaag ctgatatggc tgattagtcg gaagcatcga acgctgat                    48
```